US00PP20512P3

(12) United States Plant Patent
Hatch

(10) Patent No.: US PP20,512 P3
(45) Date of Patent: Dec. 1, 2009

(54) ***CAREX* PLANT NAMED 'REKOHU SUNRISE'**

(50) Latin Name: *Carex trifida*
Varietal Denomination: REKOHU SUNRISE

(76) Inventor: Lindsey Hatch, 78 Jericho Road, Pukekohe (NZ)

( * ) Notice: Subject to any disclaimer, the term of this patent is extended or adjusted under 35 U.S.C. 154(b) by 10 days.

(21) Appl. No.: 12/221,153

(22) Filed: Jul. 30, 2008

(65) Prior Publication Data

US 2009/0044302 P1 Feb. 12, 2009

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para

(57) ABSTRACT

A new and distinct cultivar of *Carex* named 'REKOHU SUNRISE' that is characterized by clumping habit, variegated foliage with golden-yellow edges, and chestnut-brown spikelets. In combination these traits set 'REKOHU SUNRISE' apart from all other existing varieties of *Carex* known to the inventor.

3 Drawing Sheets

Genus: *Carex*.
Species: *trifida*.
Denomination: 'REKOHU SUNRISE'.

BACKGROUND OF THE INVENTION

This application claims the benefit of priority under 35 U.S.C. 119(f) of the earlier application for New Zealand Plant Breeders Rights, Application Number GR001 filed Aug. 6, 2007.

The present invention relates to a new variety of sedge grown for use in container, border, rock garden, or the landscape. The new invention from the family Cyperaceae is known botanically as *Carex trifida* and will be referred to hereinafter as 'REKOHU SUNRISE'.

The new *Carex* cultivar named 'REKOHU SUNRISE' was discovered as a chance seedling in and amongst a commercially growing crop of *Carex trifida*. The parent is an individual *Carex trifida*. The inventor discovered the new cultivar named 'REKOHU SUNRISE' October 1992 at the inventor's nursery in Auckland, New Zealand.

'REKOHU SUNRISE' exhibits clumping habit, variegated foliage that is green with golden-yellow edges, and chestnut-brown spikelets. The new variety is 0.6 m. in height and 0.6 m. in spread the first year, reaching 0.6 m. in height and 0.8 m. in spread at maturity. Cultural requirements include free-draining soil, shade to filtered sunlight, and moderate water. The new variety 'REKOHU SUNRISE' has no disease or pest resistance known to the inventor. Plant is hardy in USDA Zones 8–11. Disease and pest susceptibility of 'REKOHU SUNRISE' is similar to the species.

The closest comparison plant is *Carex trifida*. The new *Carex* variety named 'REKOHU SUNRISE' is distinguishable from the comparison plant by unique variegated foliage with golden-yellow edges.

The first asexual reproduction of 'REKOHU SUNRISE' was conducted in March 1994 at the inventor's nursery in Auckland, New Zealand. The method used was division. In September 1995 the inventor conducted asexual propagation using the method of tissue culture. Eleven generations of asexual propagation have been carried out since 1995. Under careful observation 'REKOHU SUNRISE' has been determined fixed, stable and true to type in subsequent generations of asexual propagation.

SUMMARY OF THE INVENTION

The following traits have been repeatedly observed and represent the distinguishing characteristics of the new *Carex* cultivar named 'REKOHU SUNRISE'. These traits in combination distinguish 'REKOHU SUNRISE' from all other existing varieties of *Carex* known to the inventor. 'REKOHU SUNRISE' has not been tested under all possible conditions. Phenotypic differences may be observed with variations in environmental, climatic, and cultural conditions without however any variance in genotype.

1. 'REKOHU SUNRISE' exhibits clumping habit.
2. 'REKOHU SUNRISE' exhibits unique variegated foliage with golden-yellow edges.
3. 'REKOHU SUNRISE' exhibits chestnut-brown spikelets.
4. 'REKOHU SUNRISE' reaches a maximum of 0.6 m. in height. And 0.8 m. in width at maturity.
5. 'REKOHU SUNRISE' is asexually propagated by methods of division and tissue culture.
6. 'REKOHU SUNRISE' is hardy in USDA Zones 8–11.

BRIEF DESCRIPTION OF THE DRAWINGS

The accompanying color drawings illustrate the overall appearance of the new *Carex* cultivar named 'REKOHU SUNRISE' showing color as true as is reasonably possible to obtain in color reproductions of this type. Color in the drawings may differ from color values cited in the detailed botanical description, which accurately describe the actual color of the new variety 'REKOHU SUNRISE'.

Drawing labeled

Drawing labeled

Drawing labeled

Figure 1:
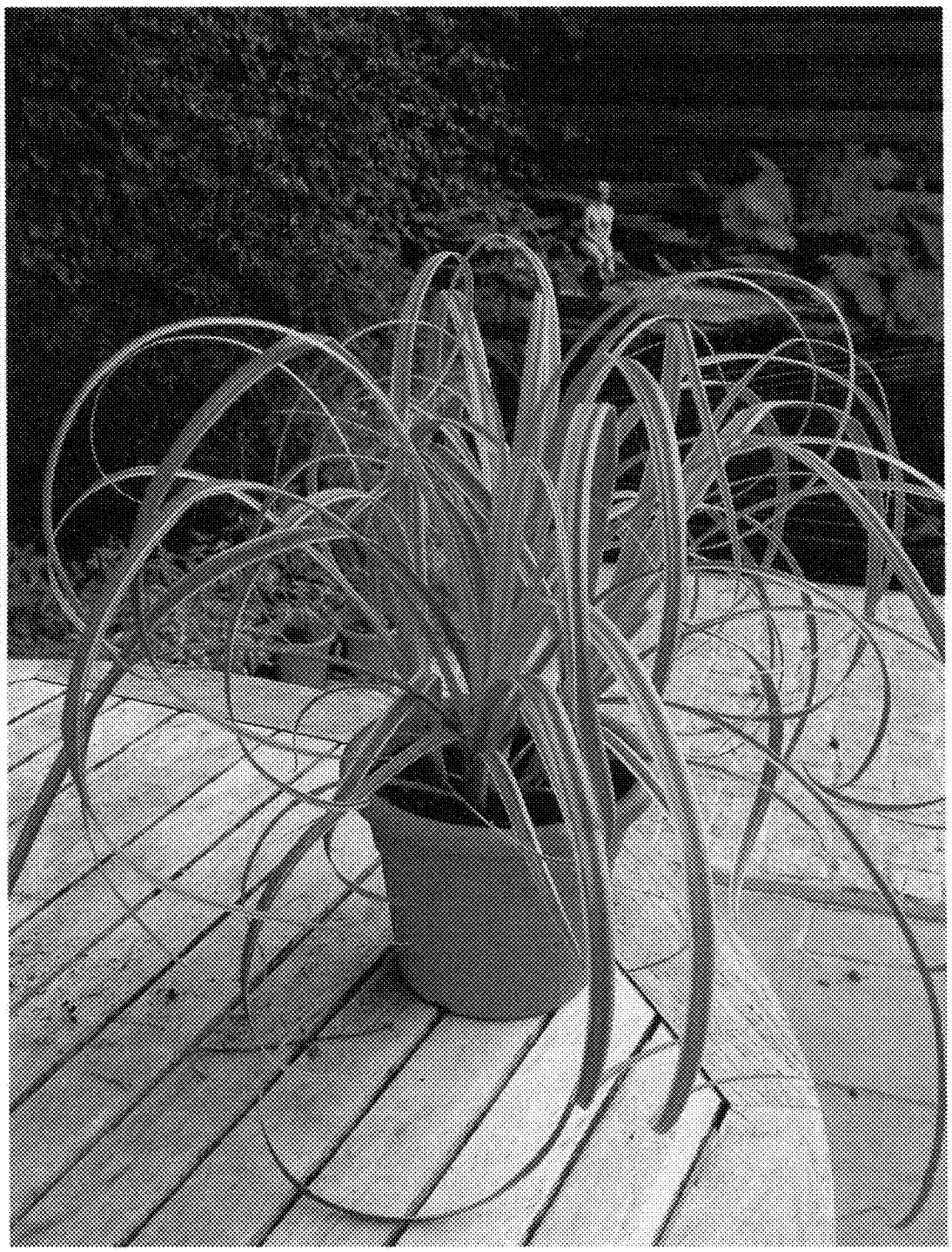
FIG. 1 depicts the plant from a side perspective illustrating the variegated foliage.
Figure 2:
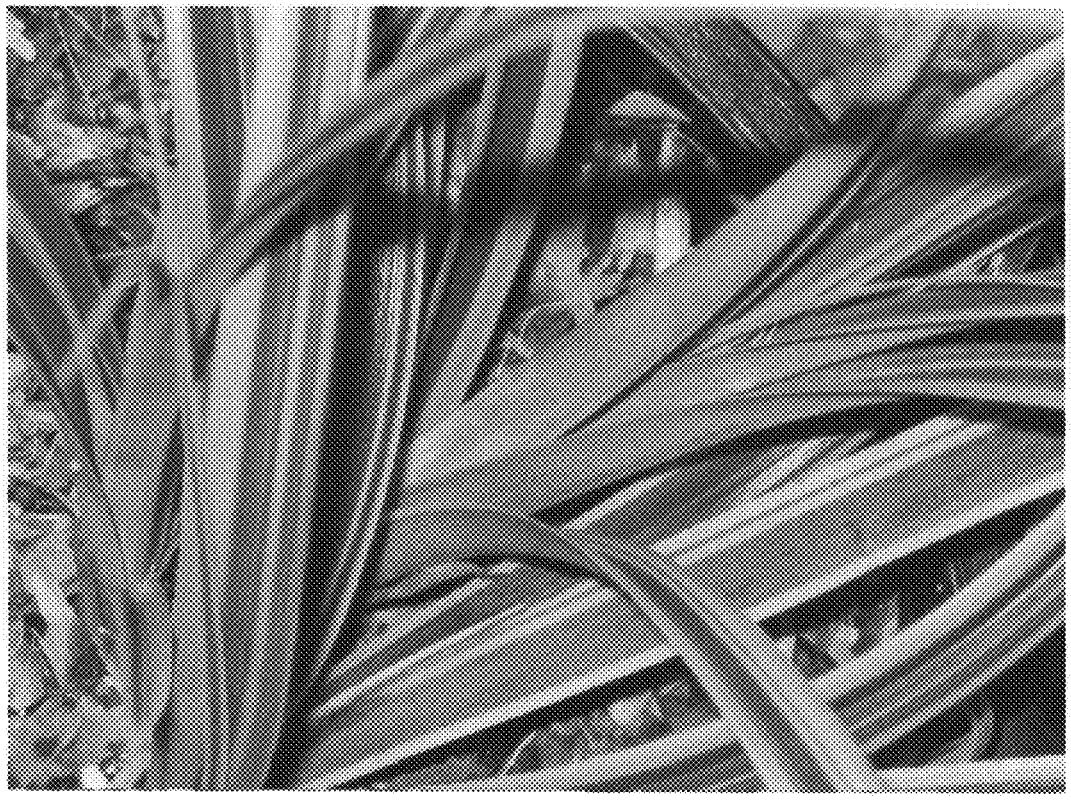
FIG. 2 depicts a close-up of the foliage.
Figure 3:
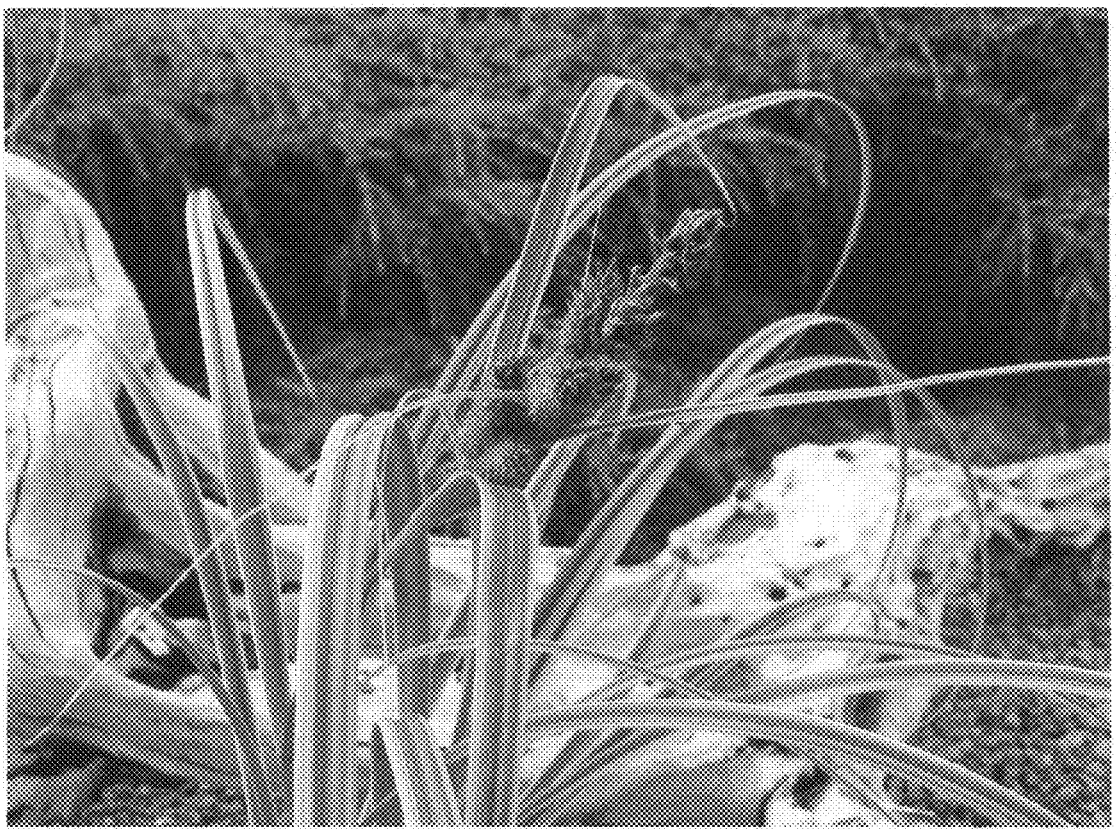
FIG. 3 depicts the spikelets.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Carex* cultivar named 'REKOHU SUNRISE'. Observations, measurements, values and comparisons were collected in Arroyo Grande, Calif., from 12-month-old plants in 1-litre containers. Color determinations are made in accordance with the 2001 Royal Horticultural Society Colour Chart from London, England, except where general color terms of ordinary dictionary significance are used. The growing requirements of the new variety 'REKOHU SUNRISE' are similar to the species.

Botanical classification: *Carex trifida* 'REKOHU SUNRISE'.
Family: Cyperaceae.
Genus: *Carex*.
Species: *Trifida*.
Denomination: 'REKOHU SUNRISE'.
Common name: Sedge.
Habit: Clumping habit.
Commercial category: Grass-like perennial herb.
Use: For container, border, rock garden, or the landscape.
Suggested commercial container size: 1-litre container.
Parentage: *Carex trifida* 'REKOHU SUNRISE' is a chance seedling discovered in and amongst a commercially growing crop of *Carex trifida*. The parent is an individual *Carex trifida*.
Propagation method: Division and tissue culture.
Rooting system: Short fibrous roots.
Vigor: Moderate.
Crop time (range): 9–12 months to produce a 1-litre container from stem cuttings.
Temperature (range): The recommended air temperature is 20–21° Centigrade.
Plant dimensions (first year): 0.6 m. in height and 0.6 m. in width.
Plant dimensions (at maturity): 0.6 m. in height and 0.8 m. in width.
Plant shape: Fountain.
Cultural requirements: Grow in well draining soil, shade to filtered sunlight, with moderate water.
Pest or disease resistance: None known to inventor.
Pest or disease susceptibility: Similar to the species.
Hardiness: USDA Zones 8–11.
Foliage:
- *Type.*—Evergreen.
- *Arrangement.*—Basal.
- *Division.*—Simple.
- *Attachment.*—Sheathing.
- *Ligule.*—None observed.
- *Margin* (*range*).—Entire and scabrid.
- *Abaxial surface* (*range*).—Glabrous and scabrid.
- *Adaxial surface.*—Glabrous.
- *Shape.*—Linear and keeled.
- *Length* (*range*).—28–35 cm.
- *Width* (*average*).—1.25 cm.
- *Color* (*abaxial surface*).—Between 189A and 162A.
- *Color* (*adaxial surface*).—Between 139A and 162B.
- *Apex.*—Cirrose.
- *Base.*—Truncate.
- *Venation.*—Parallel.
- *Vein color* (*abaxial surface*).—Between 139A and 162B.
- *Vein color* (*adaxial surface*).—Between 139A and 162B.
- *Leaf fragrance.*—None observed.

Inflorescence:
- *Inflorescence.*—Spikelet.
- *Inflorescence shape.*—Cylindric.
- *Inflorescence quantity* (*range*).—4–6 per 1 liter container.
- *Inflorescence color.*—Chestnut-brown.
- *Inflorescence aspect* (*range*).—Erect to nodding.
- *Inflorescence dimensions* (*average*).—12 cm. in length and 2 cm. in diameter.

The invention claimed is:

1. A new and distinct cultivar of *Carex* plant named 'REKOHU SUNRISE' as described and illustrated herein.

* * * * *